(12) United States Patent
Yamamoto et al.

(10) Patent No.: US 8,518,432 B2
(45) Date of Patent: Aug. 27, 2013

(54) BLOCK-SHAPED SCAFFOLD FOR TISSUE ENGINEERING AND PRODUCTION METHOD THEREOF

(75) Inventors: Katsushi Yamamoto, Tokyo (JP); Katsuyuki Yamanaka, Tokyo (JP); Youko Suda, Tokyo (JP); Tadashi Kaneko, Tokyo (JP)

(73) Assignee: GC Corporation, Tokyo (JP)

( * ) Notice: Subject to any disclaimer, the term of this patent is extended or adjusted under 35 U.S.C. 154(b) by 1101 days.

(21) Appl. No.: 12/488,862

(22) Filed: Jun. 22, 2009

(65) Prior Publication Data

US 2009/0261492 A1    Oct. 22, 2009

Related U.S. Application Data

(62) Division of application No. 11/241,997, filed on Oct. 4, 2005, now abandoned.

(30) Foreign Application Priority Data

Oct. 15, 2004    (JP) .................................. 2004-301796

(51) Int. Cl.
*A01N 25/34*    (2006.01)

(52) U.S. Cl.
USPC ........................................................ 424/426

(58) Field of Classification Search
USPC ........................................................ 424/426
See application file for complete search history.

(56) References Cited

U.S. PATENT DOCUMENTS

| 5,866,155 | A | 2/1999 | Laurencin et al. |
| 6,454,811 | B1 | 9/2002 | Sherwood et al. |
| 2006/0030627 | A1 | 2/2006 | Yamamoto et al. |
| 2007/0233277 | A1 | 10/2007 | Yamamoto et al. |
| 2009/0186412 | A1 | 7/2009 | Yamanaka et al. |

FOREIGN PATENT DOCUMENTS

| EP | 1 234 587 A1 | 8/2002 |
| EP | 1 621 216 A2 | 2/2006 |
| JP | 10-234644 | 9/1998 |
| JP | 2002-541925 | 12/2002 |
| WO | WO 00/62829 | 10/2000 |

OTHER PUBLICATIONS

Cai et al. (2002). A novel porous cells scaffold made of polylactide—dextran blend by combining phase-separation and particle-leaching techniques. Biomaterials, vol. 23, pp. 4483-4492.*
Kawanishi et al. (2004). New type of biodegradable porous scaffolds for tissue-engineered articular cartilage. Materials Science and Engineering C, vol. 24, pp. 431-435.*
Yoon et al., Degradation behaviors of biodegradable macroporous scaffoids prepared by gas foaming of effervescent salts, Journal of Biomedical Material Research, vol. 55, pp. 401-408.
U.S. Appl. No. 12/415,285, filed Mar. 31, 2009, Yamamoto, et al.
U.S. Appl. No. 12/401,121, filed Mar. 10, 2009, Yamanaka, et al.

* cited by examiner

*Primary Examiner* — Joh P Weber
*Assistant Examiner* — Kailash C Srivastava
(74) *Attorney, Agent, or Firm* — Oblon, Spivak, McClelland, Maier & Neustadt, L.L.P.

(57) ABSTRACT

A block-shaped scaffold for a tissue engineering with improved shape stability and less volume change in water is produce by the steps of approximate-uniformly mixing the particle-shaped material having 100 to 2000 μm diameter with a solution, where a biodegradable polymer is dissolved with an organic solvent, freezing, drying it to remove the solvent, pulverizing thus obtained intermediate product, dissolving it with a liquid, where the biodegradable polymer is not dissolved, to remove the particle-shaped material taking thus obtained intermediate product into a mold, and pressing and heating it, the scaffold having ununiform and continuous holes occupying 20 to 80% in a cross-section area in a three-dimensional network structure having a small hole structure with 5 to 50 μm diameter, elastic coefficient being 0.1 to 2.5 MPa, and volume change being 95 to 105% when dipping it in water for 24 hours.

8 Claims, 2 Drawing Sheets

BLOCK-SHAPED SCAFFOLD FOR TISSUE ENGINEERING AND PRODUCTION METHOD THEREOF

BACKGROUND OF THE INVENTION

1. Field of the Invention

The present invention relates to a block-shaped scaffold for a tissue engineering, which comprises a bioabsorbable polymer material, and a production method thereof. The bioabsorbable polymer material has a porous structure used as a substitute for a biotissue, excellent shape stability, and little volume change even when dipping it in water.

2. Description of the Conventional Art

For regenerating a biotissue lost by an operation, an external injury or the like, the medical treatment which has been carried out conventionally, comprises, reconstructing the lost biotissue by somatic cells, stem cells or the like, and transplanting it to a patient. In the medical treatment, a scaffold until seeded cells reconstruct the biotissue (matrix) becomes important for regenerating the biotissue.

For example, in a regeneration field of a skin or the like, the treatment comprising, producing a collagen material having a porous structure, seeding epidermic cornification cells to the collagen material, and thereby producing a cultured artificial skin having a structure of epidermis and dermis, is known. The collagen has excellent biocompatibility, and is decomposed and absorbed after regenerating the tissue, and thus the collagen is an excellent scaffold. However, as for the scaffold produced with the collagen, there are problems that the scaffold cannot keep a necessary shape since only a very soft scaffold is produced. Further, a material originating in the biology has a problem in safety with respect to an unknown pathogen when it is used as a medical supply with respect to a human body. Such an unknown pathogen is represented by BSE (bovine spongiform encephalopathy).

On the other hand, a sponge-shaped scaffold for a tissue engineering having a hole diameter of about 5 to 100 µm is used, where the scaffold is produced by the steps of dissolving a bioabsorbable polymer material (it is also said to as a biodegradable polymer) with an organic solvent such as dioxane, dichloromethane or the like, and freezing and drying this solution, where the bioabsorbable polymer material comprises lactic acid, glycolic acid, caprolactone or the like (refer to Japanese Patent Application Laid Open No. 10-234844 (1998)). Further, a bioabsorbable polymer material having a porous structure is used as the scaffold for cells, where the material has a circular opening large hole being about 50 to 500 µm and a circular opening small hole being 20 µm or less. When producing such the sponge-shaped scaffold for the tissue engineering, the bioabsorbable polymer material is produced by the steps of taking a water-soluble and nontoxic material having a particle-shape (for example, a sodium chloride powder) into a solution, where the particle diameter is about 50 to 500 µm, removing a solvent to thereby produce a biodegradable polymer containing the particle-shaped material, and removing the particle-shaped material using water or the like (for example, refer to Japanese translation of PCT international application No. 2002-541925). However, such the scaffold comprising the biodegradable polymer having the porous structure has problem that, since this scaffold is a sponge-shaped block, it has low elastic coefficient, so that it cannot keep the necessary shape in many cases. In addition, when the hole diameter is decreased in order to increase the elastic coefficient, a function as the scaffold for efficiently regenerating the biotissue is decreased.

As the other method for increasing the elastic coefficient of the biodegradable polymer, the method comprising, pressing and heating the sponge-shaped scaffold for the tissue engineering to thereby increase the density, can be used. However, the scaffold produced by this method has a problem that it is expanded with water content such as a culture medium when dipping it in a cell culture on a body fluid or the like when embedding it in a living body.

SUMMARY OF THE INVENTION

The primary objective of the present invention is to provide a block-shaped scaffold for a tissue engineering and a production method thereof, where the scaffold comprises the bioabsorbable polymer material having the porous structure and high elastic coefficient, where it is used as the scaffold until the cells seeded for regenerating the biotissue reconstruct the biotissue. Since this scaffold has the high elastic coefficient as compared with that of the conventional sponge-shaped scaffold for the tissue engineering, it has the excellent shape stability and little volume change even when absorbing the water content, and thus it is the excellent scaffold.

The earnest work was carried out in order to solve the above-mentioned problems and, as a result of this, the following cause by which the conventional sponge-shaped scaffold for the tissue engineering is expanded with the water content such as the culture medium, the body fluid or the like is found out. Since a partition wall is pressed and heated in order to increase the elastic coefficient of the scaffold while forming an integrated structure, the compression stress is easily stored in the produced scaffold. The stress is released to expand the scaffold when the partition wall is wet by the water content such as the body fluid. Then, it has been found out to complete the present invention that, when the partition wall of the hole formed in the conventional sponge-shaped bioabsorbable polymer material is once broken and thereafter, the partition wall is reformed by pressing and heating, an excellent block-shaped scaffold for the tissue engineering can be obtained. This scaffold has the excellent shape stability and the little volume change even when absorbing the water content, as compared with the case when pressing and heating the sponge-shaped bioabsorbable polymer material as it is.

That is, the present invention is the block-shaped scaffold for the tissue engineering, which comprises the bioabsorbable polymer material having ununiform and continuous holes occupying 20 to 80% in a cross-section area in a three-dimensional network structure which has a small hole structure with the hole diameter of 5 to 50 µm. In this scaffold, the elastic coefficient is 0.1 to 2.5 MPa, and a volume change is 95 to 105% when dipping it in water for 24 hours. As for the bioabsorbable polymer, it is preferable to select at least one kind from following polymers, that is, polyglycolic acid, polylactic acid, a copolymer of lactic acid and glycolic acid, poly-ε-caprolactone, a copolymer of lactic acid and ε-caprolactone, polyamino acid, polyortho ester, and a copolymer of those.

Further, the production method of the block-shaped scaffold for the tissue engineering comprises, approximate-uniformly mixing a particle-shaped material having the particle diameter of 100 to 2000 µm with a solution in which a bioabsorbable polymer is dissolved with an organic solvent where the particle-shaped material is not dissolved with the organic solvent but dissolved in a liquid in which the bioabsorbable polymer is not dissolved, freezing it, drying it, and removing the organic solvent. Thereby, a polymer material containing the particle-shaped material is produced, where the polymer material has the small hole structure having the hole diameter of 5 to 50 μm. The polymer material is pulverized, dissolved in a liquid in which the bioabsorbable polymer is not dissolved, to remove the particle-shaped material, and passed it through a sieve. Thus, a bioabsorbable granular porous material having the particle diameter of 100 to 3000 μm is produced. Then the bioabsorbable granular porous material is taken into a mold to be pressed and heated, thereby producing the block-shaped scaffold for the tissue engineering, which has ununiform and continuous holes occupying 20 to 80% in the cross-section area in the three-dimensional network structure having the small hole structure with the hole diameter of 5 to 50 μm. In this scaffold, the elastic coefficient is 0.1 to 2.5 MPa, and the volume change is 95 to 105% when dipping it in water for 24 hours.

The followings are also found out in the production method of the block-shaped scaffold for the tissue engineering. That is, as for the bioabsorbable polymer material, it is also preferable to select at least one kind from following polymers, that is, polyglycolic acid, polylactic acid, a copolymer of lactic acid and glycolic acid, poly-ε-caprolactone, a copolymer of lactic acid and ε-caprolactone, polyamino acid, polyortho ester, and a copolymer of those. As for the organism solvent, it is preferable to select at least one kind from chloroform, dichloromethane, carbon tetrachloride, acetone, dioxane, and tetrahydrofuran. As for the conditions for taking the bioabsorbable granular porous material into the mold, and pressing and heating it, it is preferable that the bioabsorbable granular porous material is heated at 60 to 200° C. while keeping the volume in the state of being pressed at 500 to 3000 g/cm².

The block-shaped scaffold for the tissue engineering produced by the production method according to the present invention is the scaffold for the tissue engineering comprising the bioabsorbable polymer material having the porous structure, which is the scaffold until seeded cells reconstruct the biotissue, where the seeded cells is seeded for regenerating the biotissue. The block-shaped scaffold for the tissue engineering has the excellent shape stability and the little volume change even when absorbing the water content, as compared with those of the conventional sponge-shaped scaffold for the tissue engineering.

DETAILED DESCRIPTION OF PREFERRED EMBODIMENT

Figure 1:
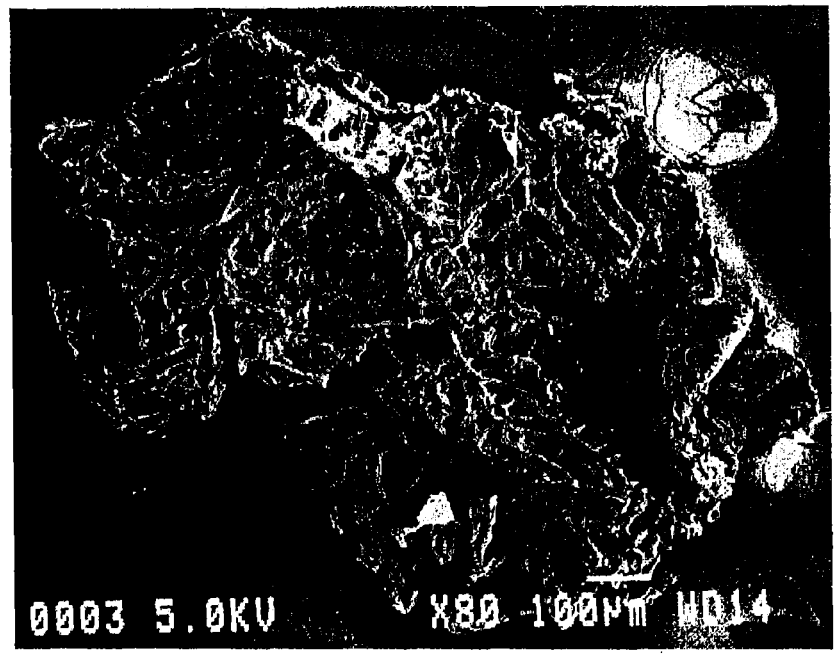
FIG. 1 is a scanning electron microscope photograph of a bioabsorbable granular porous material used for producing a block-shaped scaffold for a tissue engineering in Example 1.

When the biodegradable polymer used in the present invention is safe for a living body, can keep the shape in the body during a fixed period, and can not be dissolved with the solution which can dissolve the particle-shaped material, as mentioned below, the polymer can be used without the especial limitation. For example, at least the one kind selected from the followings can be used, that is, polyglycolic acid, polylactic acid, a copolymer of lactic acid and glycolic acid, poly-ε-caprolactone, a copolymer of lactic acid and ε-caprolactone, polyamino acid, polyortho ester, and a copolymer of those. In these materials, polyglycolic acid, polylactic acid, and the copolymer of lactic acid and glycolic acid are the most preferable since these are recognized from U.S. Food and Drug Administration (FDA) as the polymer being harmless to a human body, and have actual results. It is preferable that the weight-average molecular weight of the bioabsorbable polymer is 5,000 to 2,000,000, and more preferably 10,000 to 500,000.

In the production method of the block-shaped scaffold for the tissue engineering according to the present invention, the biodegradable polymer is dissolved with the organic solvent in the producing process. Although the organic solvent is used suitably selecting with the biodegradable polymer material to be used, at least one kind selected form the followings is preferably used in general, that is, chloroform, dichloromethane, carbon tetrachloride, acetone, dioxane, and tetrahydrofuran. In the dissolving process, a heat treatment or an ultrasonic treatment may be used together. Although the concentration of the biodegradable polymer is not limited especially if this polymer can be dissolved uniformly in the organic solvent, it is preferable that the concentration is 1 to 20% by weight in the organic solvent.

In the production method of the block-shaped scaffold for the tissue engineering according to the present invention, the particle-shaped material having the particle diameter of 100 to 2000 μm is approximate-uniformly mixed with the organic solvent dissolving the biodegradable polymer in the producing process. This particle-shaped material is not dissolved with the organic solvent but is dissolved with the liquid which does not dissolve the biodegradable polymer. The particle-shaped material can exist in the solid state in the polymer material, until the polymer material is pulverized to become once the granular material. The polymer material is produced by the steps of approximate-uniformly mixing the particle-shaped material with the solution dissolving the biodegradable polymer, freezing it, drying it, and removing the organic solvent. Thus, the polymer material contains the particle-shaped material and has the small hole structure having the hole diameter of 5 to 50 μm. Further, the particle-shaped material can be rapidly dissolved and removed with the liquid, which does not dissolve the biodegradable polymer, after pulverizing. The biodegradable polymer becomes hard since the particle-shaped material exists in the solid state (in the particle state) in the biodegradable polymer, so that the pulverization becomes easy, and thus, the granule having the arbitrary particle diameter can be easily produced.

As the method for approximate-uniformly mixing the particle-shaped material with the organic solvent dissolving the biodegradable polymer, the following methods can be used. That is, a method comprising, taking the particle-shaped material into the organic solvent dissolving the biodegradable polymer, stirring and mixing it if necessary, and taking it into a mold, a method comprising, taking the organic solvent dissolving the biodegradable polymer into a mold where the particle-shaped material is already put in, or a method comprising, mixing the particle-shaped material into a mold where the organic solvent dissolving the biodegradable polymer is already put in.

In the production method of the block-shaped scaffold for the tissue engineering according to the present invention, it is necessary that the particle diameter of the particle-shaped material is 100 to 2000 μm, where the particle-shaped material is approximate-uniformly mixed with the organics solvent dissolving the biodegradable polymer, and an aggregated granular crystalline particle may be used if it is a crystalline material. If the particle diameter of the particle-shaped material is less than 100 μm, the density of the produced block-shaped scaffold for the tissue engineering becomes too high, since a space between granules is small, where the granules is produced by pulverizing the polymer containing the particle-shaped material to have the granular state, dissolving, and removing the particle-shaped material with the liquid which does not dissolve the biodegradable polymer. Thus, a necessary number of the cells cannot be cultured in the block-shaped scaffold for the tissue engineering. If the particle diameter is more than 2000 μm, since the space between the granules is large, this large space is broken by pressing and heating, where the granules is produced by pulverizing the polymer containing the particle-shaped material to have the granular state, dissolving, and removing the particle-shaped material with the liquid which does not dissolve the biodegradable polymer. As a result of this, the density of the produced block-shaped scaffold for the tissue engineering becomes too high, and thus the necessary numbers of the cells cannot be cultured in the block-shaped scaffold for the tissue engineering. Preferably, the particle diameter is 200 to 1000 μm.

Further, it is preferable that the blending amount of the particle-shaped material to the organic solvent dissolving the biodegradable polymer is 1.0 to 1.5 g/cm$^3$. If the blending amount is less than 1.0 g/cm$^3$, the effect for hardening the biodegradable polymer as an intermediate product is hardly obtained. If this amount is more than 1.5 g/cm$^3$, the ratio of the polymer in the polymer material is decreased, so that the production yield may be decreased. More preferably, the blending amount is 1.0 to 1.25 g/cm$^3$.

In the production method of the block-shaped scaffold for the tissue engineering according to the present invention, it is possible to obtain the bioabsorbable granular porous material having the arbitrary particle diameter by pulverizing the polymer material, dissolving the particle-shaped material to be removed with the liquid which does not dissolve the biodegradable polymer, and passing it thorough the sieve. Thus, the bioabsorbable granular porous material having the particle diameter of 100 to 3000 μm is produced. The reason why the particle diameter of the bioabsorbable granular porous material is 100 to 3000 μm is the followings. That is, if the particle diameter is less than 100 μm, the ununiform and continuous holes do not occupy 20% or more in the cross-section area, so that it is not preferable. Further, if the particle diameter is more than 3000 μm, the number of the ununiform and continuous holes is too few to occupy 80% or less in the cross-section area, so that it is not preferable. At this time, although a method for removing the particle-shaped material is changed with the material, if the water soluble organic and/or inorganic salt is used as described above, the material can be removed easily and safety with water, where the salt is, for example, sodium chloride, potassium chloride, calcium chloride, ammonium chloride, trisodium citrate or the like.

In the production method of the block-shaped scaffold for the tissue engineering according to the present invention, when the bioabsorbable granular porous material is taken into the desired mold, pressed and heated, the block-shaped scaffold for the tissue engineering having the specific shape is produced, where the scaffold has the ununiform and continuous holes occupying 20 to 80% in the cross-section area in the three-dimensional network structure having the small hole structure with the hole diameter of 5 to 50 μm. In this scaffold, the elastic coefficient is 0.1 to 2.5 MPa, and the volume change is 95 to 105% when dipping it in water for 24 hours. The reason why the block-shaped scaffold for the tissue engineering must have the small hole structure with the hole diameter of 5 to 50 μm is as follows. That is, if the hole diameter is less than 5 μm, it is hard to smoothly move the body fluid or the like passing through the partition wall, so that it is not preferable. If the hole diameter is more than 50 μm, the strength of the partition wall is decreased, so that the desired elastic coefficient may not be obtained. Further, the reason why the ununiform and continuous holes must occupy 20 to 80% in the cross-section area in the three-dimensional network structure is as follows. That is, if the holes occupy less than 20%, there are too little amount of the ununiform and continuous holes, the number of the cells in the block-shaped scaffold for the tissue engineering is decreased to produce an insufficient scaffold, so that it is not preferable. If the holes occupy more than 80%, the ununiform and continuous holes become large, and the cells are not stored in the scaffold to decrease the function as the scaffold, so that it is not preferable. Further, the reason why the elastic coefficient must be 0.1 to 2.5 MPa is as follows. That is, if the elastic coefficient is less than 0.1 MPa, the scaffold is deformed when gripping it by a pincette or the like and transferring it to an affected part of a patient, or deformed in the living body, so that it is not preferable. If the elastic coefficient is more than 2.5 MPa, it is hard to carry out an operation for deforming the scaffold according to a deficit of a patient, so that it is not preferable. Further, the reason why the volume change is 95 to 105% when dipping the scaffold in water for 24 hours, is that the scaffold is not expanded and contracted by the culture liquid at the time of the cell culture, or the body fluid or a blood at the time of putting it on the affected part of a patient. Such the characteristics are specific ones which cannot be obtained only by pressing and heating the conventional sponge-shaped block body.

It is preferable that the pressing condition is 500 to 3000 g/cm$^2$, although it is changed with the material, the shape or the size of the bioabsorbable granular porous material. If it is less than 500 g/cm$^2$, the shape stability of the block-shaped scaffold for the tissue engineering may be insufficient. If it is more than 3000 g/cm$^2$, the holes, in which the cells can be proliferated, hardly remain. More preferably, the pressing condition is 1000 to 2000 g/cm$^2$. Further, if the pressing condition is out of this range, the volume change is increased when contacting with water.

Although the heating condition is also changed with the material, the shape or the size of the bioabsorbable granular porous material, if the heating is carried out while keeping the volume in the state of the above pressing condition, it may be within the range of 60 to 200° C. If it is less than 60° C., the bonding of the granular biodegradable porous polymers becomes weak. Thus, it is hard to form the block shape, or the shape stability becomes insufficient since the elastic coefficient of the block-shaped scaffold for the tissue engineering is remarkably decreased. On the other hand, if it is more than 200° C., the granular biodegradable porous polymer may be denatured.

EXAMPLES

Example 1

Figure 2:
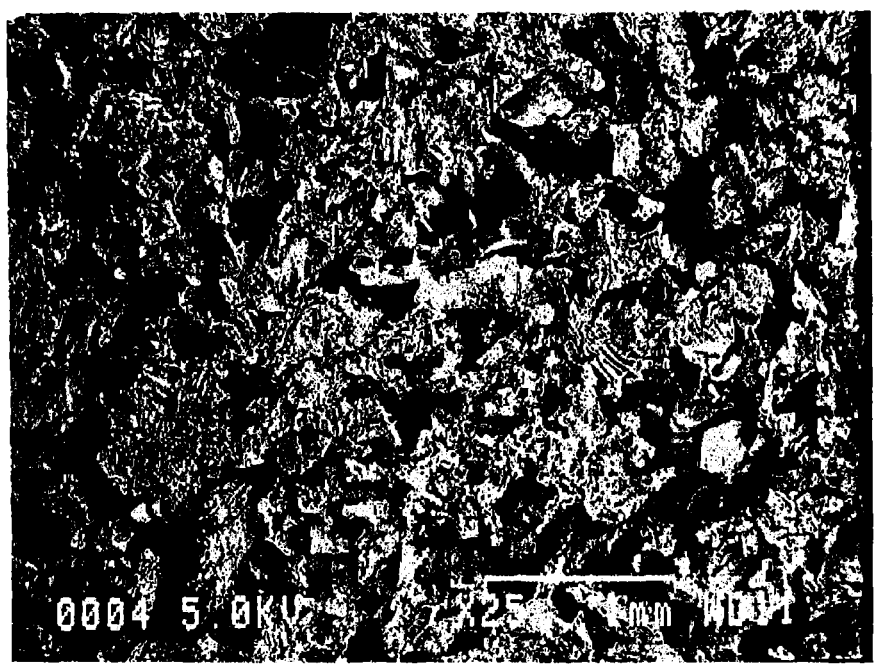
FIG. 2 is a scanning electron microscope photograph of the block-shaped scaffold for the tissue engineering produced in Example 1.

The polymer material approximate-uniformly containing a sodium chloride powder was obtained by the steps of taking the copolymer of lactic acid and glycolic acid (lactic acid: glycolic acid=75:25, the weight average molecular weight was about 250,000) into dioxane to have the concentration of 12% by weight, stirring it by a stirrer to dissolve it, approximate-uniformly mixing the sodium chloride powder (a particle diameter was 300 to 700 μm) with the dioxane solution dissolving the copolymer of lactic acid and glycolic acid to have the sodium chloride concentration of about 1.18 g/cm$^3$, taking it into the mold, freezing it under the condition of −30° C. by a freezer (MDF-0281AT made by Sanyo Electric Corporation), and drying it under a reduced atmosphere for 48 hours by a vacuum dryer (DP43 made by Yamato Scientific Corporation) to thereby remove the dioxane. Then, the bioabsorbable granular porous material was obtained by the steps of cutting the polymer material to become small pieces, pulverizing the small pieces by a planetary ball mill for 50 minutes, taking the pulverized polymer material into a flask, adding a distilled water to the flask, stirring it to remove sodium chloride, moving it to a petri dish, drying it in the vacuum dryer for 48 hours, and passing it through the sieve. This bioabsorbable granular porous material had the particle diameter of 300 to 700 μm and the average hole diameter of about 5 μm. The scanning electron microscope photograph of this bioabsorbable granular porous material was shown in FIG. 1. Then, the block-shaped scaffold for the tissue engineering was obtained by the steps of taking the bioabsorbable granular porous material into a glass mold having an inner diameter of 9 mm and a height of 10 mm so as to have the material height of about 8 mm, and heating at 80° C. for 30 minutes while keeping the volume in a state where it is pressed at 1500 g/cm$^2$ by a glass rod having a diameter of 9 mm. The block-shaped scaffold for the tissue engineering had the ununiform and continuous holes occupying approximately 60% in the cross-section in the three-dimensional network structure which had the small hole structure with 5 to 50 μm hole diameter at the partition wall. The block-shaped scaffold had a cylindrical shape having a diameter of 9 mm and a height of about 4 mm. The scanning electron microscope photograph of this block-shaped scaffold for the tissue engineering was shown in FIG. 2.

Example 2

The polymer material approximate-uniformly containing a sodium chloride powder was obtained by the steps of taking the polyglycolic acid (the weight average molecular weight was about 200,000) into dichloromethane to have the concentration of 9% by weight, stirring it by the stirrer to dissolve it, taking the dichloromethane solution dissolving polyglycolic acid into a mold where the sodium chloride powder (the particle diameter was 300 to 700 μm) was already put in to have sodium chloride concentration of about 1.18 g/cm$^3$, freezing it under the condition of −30° C. by the freezer (MDF-0281AT made by Sanyo Electric Corporation), and drying it under a reduced atmosphere for 48 hours by the vacuum dryer (DP43 made by Yamato Scientific Corporation) to thereby remove dichloromethane. Then, the bioabsorbable granular porous material was obtained by the steps of cutting the polymer material to become small pieces, pulverizing the small pieces by the planetary ball mill for 20 minutes, taking the pulverized polymer material into the flask, adding the distilled water to the flask, stirring it to thereby remove sodium chloride, moving it to the petri dish, drying it by the vacuum dryer for 48 hours, and passing it through the sieve. This bioabsorbable granular porous material had the particle diameter of 700 to 1400 μm and the average hole diameter of about 5 μm. Thereafter, the block-shaped scaffold for the tissue engineering was obtained by the steps of taking the bioabsorbable granular porous material into the glass mold having the inner diameter of 9 mm and the height of 10 mm so as to have the material height of about 7 mm, and heating it at 160° C. for 30 minutes while keeping the volume in the state where it is pressed at 1500 g/cm$^2$ by the glass rod having the diameter of 9 mm. The block-shaped scaffold for the tissue engineering had ununiform and continuous holes occupying approximately 60% in the cross-section in the three-dimensional network structure, which had the small hole structure with 5 to 50 μm hole diameter the partition wall. The block-shaped scaffold had the cylindrical shape having the diameter of 9 mm and the height of about 4 mm.

Example 3

The polymer material approximate-uniformly containing a potassium chloride powder was obtained by the steps of taking the copolymer of lactic acid and glycolic acid (lactic acid:glycolic acid=75:25, the weight average molecular weight was about 250,000) into dioxane to have the concentration of 12% by weight, stirring it by the stirrer to dissolve it, taking the dioxane solution dissolving the copolymer of lactic acid and glycolic acid into the mold where the potassium chloride powder (the particle diameter was about 400 μm) is already put in to have the potassium chloride concentration of about 1.08 g/cm$^3$, freezing it under the condition of −30° C. by the freezer (MDF-0281AT made by Sanyo Electric Corporation), and drying it under a reduced atmosphere for 48 hours by the vacuum dryer (DP43 made by Yamato Scientific Corporation) to thereby remove dioxane. Then, the bioabsorbable granular porous material was obtained by the steps of cutting the polymer material to become small pieces, pulverizing the small pieces by the planetary ball mill for 50 minutes, taking the pulverized polymer material into the flask, adding the distilled water to the flask, stirring it to thereby remove potassium chloride, moving it to the petri dish, drying it by the vacuum dryer for 48 hours, and passing it through the sieve. This bioabsorbable granular porous material had the particle diameter of 300 to 700 μm, and the average hole diameter of about 5 μm. Thereafter, the block-shaped scaffold for the tissue engineering was obtained by the steps of taking the bioabsorbable granular porous material into the glass mold having the inner diameter of 9 mm and the height of 10 mm so as to have the material height of about 8 mm, and heating it at 80° C. for 30 minutes while keeping the volume in the state where it is pressed at 1500 g/cm$^2$ by the glass rod having the diameter of 9 mm. The block-shaped scaffold for the tissue engineering had the ununiform and continuous holes occupying approximately 60% in the cross-section in the three-dimensional network structure, which had the small hole structure with 5 to 50 μm hole diameter at the partition wall. The block-shaped scaffold had the cylindrical shape having the diameter of 9 mm and the height of about 4 mm.

Example 4

Figure 3:
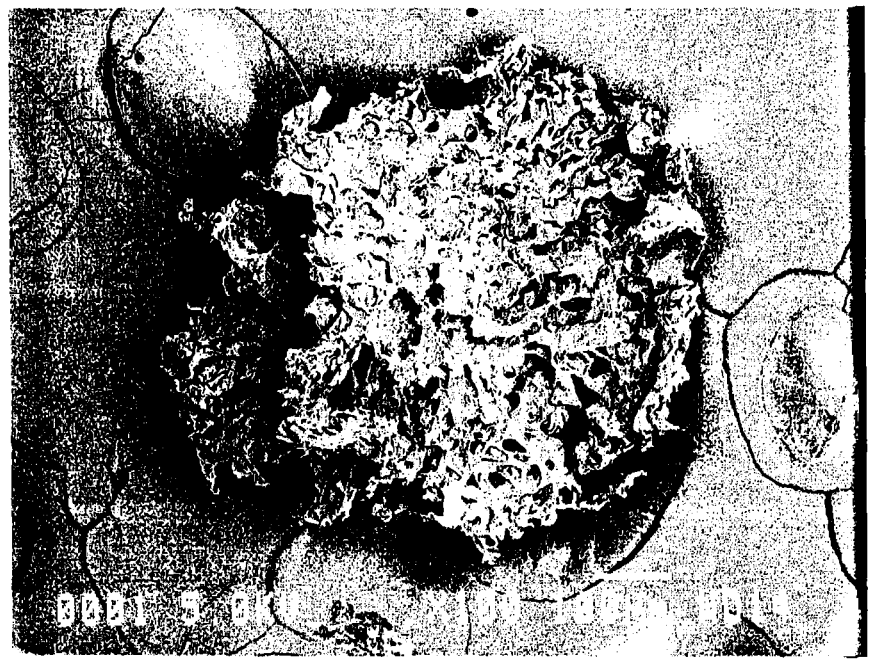
FIG. 3 is a scanning electron microscope photograph of a bioabsorbable granular porous material used for producing a block-shaped scaffold for a tissue engineering in Example 4.
Figure 4:
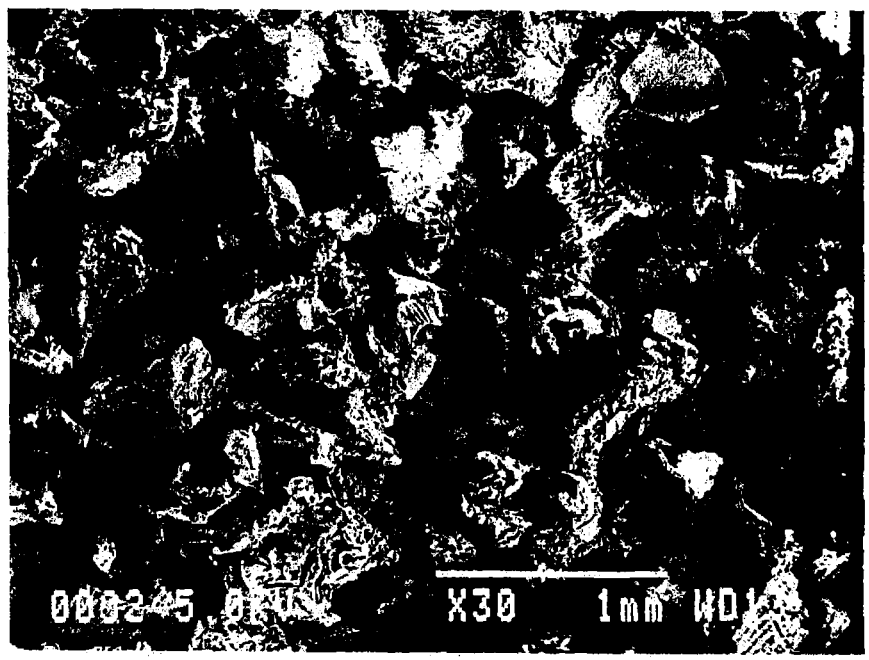
FIG. 4 is a scanning electron microscope photograph of the block-shaped scaffold for the tissue engineering produced in Example 4.

The polymer material approximate-uniformly containing a trisodium citrate powder was obtained by the steps of taking the poly-(L)-lactic acid (the weight average molecular weight was about 250,000) into dichloromethane to have the concentration of 6% by weight, stirring it by the stirrer to dissolve it, approximate-uniformly mixing the trisodium citrate powder (the particle diameter was 200 to 500 μm) with the dichloromethane solution dissolving the poly-(L)-lactic acid to have the concentration of about 1.02 g/cm$^3$, taking it into the mold, freezing it under the condition of −30° C. by the freezer (MDF-0281AT made by Sanyo Electric Corporation), and drying it under a reduced atmosphere for 48 hours by the vacuum dryer (DP43 made by Yamato Scientific Corporation) to thereby remove dichloromethane. Then, the bioabsorbable granular porous material was obtained by the steps of cutting the polymer material to become small pieces, pulverizing the small pieces by the planetary ball mill for 20 minutes, taking the pulverized polymer material into the flask, adding a distilled water to the flask, stirring it to thereby remove trisodium citrate, moving it to the petri dish, drying it by the vacuum dryer for 48 hours, and passing it through the sieve. This bioabsorbable granular porous material had the particle diameter of 700 to 1400 μm and the average hole diameter of about 5 μm. The scanning electron microscope photograph of this bioabsorbable granular porous material is shown in FIG. 3. Thereafter, the block-shaped scaffold for the tissue engineering was obtained by the steps of taking the bioabsorbable granular porous material into the glass mold having the inner diameter of 9 mm and the height of 10 mm so as to have the material height of about 7 mm, and heating it at 180° C. for 30 minutes while keeping the volume in the state where it is pressed at 1500 g/cm² by the glass rod having the diameter of 9 mm. The block-shaped scaffold for the tissue engineering had the ununiform and continuous holes occupying approximately 60% in the cross-section in the three-dimensional network structure which had the small hole structure with 5 to 50 μm hole diameter at the partition wall. The block-shaped scaffold had the cylindrical shape having the diameter of 9 mm and the height of about 4 mm. The scanning electron microscope photograph of this block-shaped scaffold for the tissue engineering was shown in FIG. 4.

Comparison Example 1

The polymer material approximate-uniformly containing the sodium chloride powder was obtained by the steps of taking the copolymer of lactic acid and glycolic acid (lactic acid:glycolic acid=75:25, the weight average molecular weight was about 250,000) into dioxane to have the concentration of 4% by weight, stirring it by the stirrer to dissolve it, approximate-uniformly mixing the sodium chloride powder (the particle diameter was 300 to 700 μm) with the dioxane solution dissolving the copolymer of lactic acid and glycolic acid to have the concentration of 1.18 g/cm³, taking it into the glass mold having the inner diameter of 9 mm and the height of 10 mm so as to have the solution height of about 5 mm, freezing it under the condition of −30° C. by the freezer (MDF-0281AT made by Sanyo Electric Corporation), and drying it under a reduced atmosphere for 48 hours by the vacuum dryer (DP43 made by Yamato Scientific Corporation) to thereby remove dioxane. Then, the bioabsorbable porous material was obtained by the steps of adding the distilled water to the polymer material to remove the sodium chloride, and drying it for 48 hours by the vacuum dryer. The bioabsorbable porous material had the average hole diameter of 300 to 700 μm, and the small hole structure of the average hole diameter of about 5 μm at the wall surface. The bioabsorbable porous material had the sponge-type cylindrical shape having the diameter of 9 mm and the height of about 4 mm.

Comparison Example 2

The polymer material approximate-uniformly containing the sodium chloride powder was obtained by the steps of taking the copolymer of lactic acid and glycolic acid (lactic acid:glycolic acid=75:25, the weight average molecular weight was about 250,000) into dioxane to have the concentration of 4% by weight, stirring it by the stirrer to dissolve it, approximate-uniformly mixing the sodium chloride powder (the particle diameter was 300 to 700 μm) with the dioxane solution dissolving the copolymer of lactic acid and glycolic acid to have the concentration of 1.18 g/cm³, taking it into the glass mold having the inner diameter of 9 mm and the height of 30 mm so as to have the solution height of about 25 mm, freezing it under the condition of −30° C. by the freezer (MDF-0281AT made by Sanyo Electric Corporation), and drying it at a reduced atmosphere for 48 hours by the vacuum dryer (DP43 made by Yamato Scientific Corporation) to thereby remove dioxane. Then, the bioabsorbable porous material was obtained by the steps adding the distilled water to the polymer material to remove the sodium chloride, and drying it for 48 hours by the vacuum dryer. This bioabsorbable porous material had the average hole diameter of 300 to 700 μm, the small hole structure of the average hole diameter of about 5 μm on the wall surface, and the sponge-type cylindrical shape having the diameter of 9 mm and the height of about 20 mm. Then, the block-shaped scaffold for the tissue engineering was obtained by the steps heating the bioabsorbable porous material taken into the glass mold at 80° C. for 30 minutes while keeping the volume in the state where it is pressed at 100 g/cm² by the glass rod having the diameter of 9 mm. This block-shaped scaffold for the tissue engineering had the small hole structure with 5 μm hole diameter at the partition wall, and the cylindrical shape having the diameter of 9 mm and the height of about 4 mm.

The following tests were carried out using the block-shaped scaffold for the tissue engineering having the cylindrical shapes of respective examples and comparison examples.

<Elastic Coefficient>

The block-shaped scaffold for the tissue engineering having the cylindrical shapes of respective examples and comparison examples were taken out from the glass mold, and a compressive load is applied in the axial direction of each cylinder. Then, the elastic coefficient was obtained from the stress and strain of each scaffold. These results were shown in Table 1 collectively.

<Volume Change by Dipping in Water>

The block-shaped scaffold for the tissue engineering having the cylindrical shapes of respective examples and comparison examples were put in the glass mold having the inner diameter of 10 mm and the height of 20 mm, and enough amounts of water for fully dipping the block-shaped scaffold were added. The volume change by dipping in water was obtained from the volume difference of the block-shaped scaffold before adding water and after 24 hours. These results were shown in Table 1 collectively.

TABLE 1

|  | Example 1 | Example 2 | Example 3 | Example 4 | Comparison example 1 | Comparison example 2 |
| --- | --- | --- | --- | --- | --- | --- |
| Elastic Coefficient (MPa) | 1.02 | 0.74 | 1.07 | 0.85 | 0.003 | 0.62 |

TABLE 1-continued

|  | Example 1 | Example 2 | Example 3 | Example 4 | Comparison example 1 | Comparison example 2 |
|---|---|---|---|---|---|---|
| Volume Change by Dipping | 101.5% | 100.4% | 101.3% | 100.9% | 57.6% | 197.5% |

Clearly from the examples, the followings are found out. That is, the block-shaped scaffold for the tissue engineering according to the present invention has the ununiform and continuous holes occupying 20 to 80% in the cross-section area in the three-dimensional network structure having the small hole structure with the hole diameter of 5 to 50 μm. This block-shaped scaffold has the excellent shape stability since having the elastic coefficient of 0.1 to 2.5 MPs, and is not expanded with the water content such as the culture medium, the body fluid or the like since having the volume change of 95 to 105%. On the other hand, as for the scaffold for the tissue engineering of the comparison example 1, the particle-shaped material is removed by dissolving with the liquid, which does not dissolve the bioabsorbable polymer, without pulverizing the polymer material produced in the producing process of the block-shaped scaffold for the tissue engineering according to the present invention. Thus, the partition wall has the sponge structure while forming the integrated structure, so that the scaffold has the remarkably low elastic coefficient and insufficient shape stability. The scaffold is easily contracted with the water content such as the culture medium, the body fluid or the like. Further, the scaffold for the tissue engineering of the comparison example 2 is obtained by pressing and heating the scaffold of the comparison example 1, where the particle-shaped material is removed by dissolving with the liquid, which does not dissolve the bioabsorbable polymer, without pulverizing the polymer material produced in the producing process of the block-shaped scaffold for the tissue engineering according to the present invention. In this scaffold, the partition wall has the sponge structure having the remarkably low elastic coefficient while forming the integrated structure. Thus, the scaffold is remarkably deformed by slight pressing, so that the density becomes high, and although the elastic coefficient becomes within the desired range, the stress stored by the pressing and heating is released for and expansion when dipping with the water content such as the culture medium, the body fluid or the like. Therefore, this scaffold cannot be used as the block-shaped scaffold for the tissue engineering.

What is claimed is:

1. A production method for a block-shaped scaffold for tissue engineering, the method comprising, approximate-uniformly mixing a particle-shaped material having a particle diameter of 100 to 2000 μm with a solution in which a bioabsorbable polymer is dissolved with an organic solvent, where the particle-shaped material is not dissolved with said organic solvent but dissolved in a liquid in which the bioabsorbable polymer is not dissolved, freezing the mixture, drying it to remove said organic solvent, and producing thereby a polymer material containing the particle-shaped material and having a small hole structure wherein a hole diameter is 5 to 50 μm; pulverizing said produced polymer material, removing said particle-shaped material by dissolving with a liquid in which the bioabsorbable polymer is not dissolved, passing through a sieve, and producing thereby a bioabsorbable granular porous material having a particle diameter of 100 to 3000 μm; and taking said bioabsorbable granular porous material into a mold, pressing and heating the bioabsorbable granular porous material, producing thereby the block-shaped scaffold for tissue engineering having ununiform and continuous holes occupying 20 to 80% in a cross-section area in a three-dimensional network structure having the small hole structure with the hole diameter of 5 to 50 μm, having an elastic coefficient of 0.1 to 2.5 MPa, and a volume change of 95 to 105% when dipping in water for 24 hours.

2. The production method of claim 1, wherein the bioabsorbable polymer material is at least one member selected from the group consisting of polyglycolic acid, polylactic acid, a copolymer of lactic acid and glycolic acid, poly-ε-caprolactone, a copolymer of lactic acid and ε-caprolactone, polyamino acid, polyortho ester, and copolymers thereof.

3. The production method of claim 1, wherein the organic solvent is at least one member selected from the group consisting of chloroform, dichloromethane, carbon tetrachloride, acetone, dioxane, and tetrahydrofuran.

4. The production method of claim 1, wherein the block-shaped scaffold for the tissue engineering is produced by heating the bioabsorbable granular porous material at 60 to 200° C. while keeping the volume in a state of being pressed at 500 to 3000 g/cm$^2$.

5. The production method of claim 2, wherein the organic solvent is at least one member selected from the group consisting of chloroform, dichloromethane, carbon tetrachloride, acetone, dioxane, and tetrahydrofuran.

6. The production method of claim 2, wherein the block-shaped scaffold for the tissue engineering is produced by heating the bioabsorbable granular porous material at 60 to 200° C. while keeping the volume in a state of being pressed at 500 to 3000 g/cm$^2$.

7. The production method of claim 3, wherein the block-shaped scaffold for the tissue engineering is produced by heating the bioabsorbable granular porous material at 60 to 200° C. while keeping the volume in a state of being pressed at 500 to 3000 g/cm$^2$.

8. The production method of claim 5, wherein the block-shaped scaffold for the tissue engineering is produced by heating the bioabsorbable granular porous material at 60 to 200° C. while keeping the volume in a state of being pressed at 500 to 3000 g/cm$^2$.

* * * * *